United States Patent [19]

Cuenca

[11] Patent Number: 5,714,124
[45] Date of Patent: Feb. 3, 1998

[54] HEMATOLOGY BLOOD DISPENSING AND SMEARING DEVICE

[76] Inventor: Hilario S. Cuenca, 31-31 55th St., Woodside, N.Y. 11377

[21] Appl. No.: 642,948

[22] Filed: May 6, 1996

[51] Int. Cl.[6] .............................. G01N 21/00; B05B 7/00
[52] U.S. Cl. ........................ 422/100; 422/67; 422/102; 422/104; 436/46; 118/100; 118/415
[58] Field of Search .................. 422/65, 66, 67, 422/100, 102, 103, 104; 436/46; 118/100, 415

[56] References Cited

U.S. PATENT DOCUMENTS

| | | | |
|---|---|---|---|
| D. 314,622 | 2/1991 | Andersson et al. | D24/53 |
| 3,880,111 | 4/1975 | Levine et al. | 118/4 |
| 3,888,206 | 6/1975 | Faulkner | 118/100 |
| 4,407,843 | 10/1983 | Sasaki et al. | 427/2 |
| 4,412,548 | 11/1983 | Hoch | 128/764 |
| 4,994,040 | 2/1991 | Cameron et al. | 604/160 |
| 5,117,837 | 6/1992 | Wanamaker et al. | 128/763 |
| 5,344,666 | 9/1994 | Levine | 427/2.11 |
| 5,356,595 | 10/1994 | Kanamori et al. | 422/65 |

*Primary Examiner*—Harold Y. Pyon

[57] ABSTRACT

A hematology blood dispensing and smearing device including a smearing member. A cannula portion is secured within the smearing member for puncturing a closed collection tube to obtain a drop of blood to be smeared onto a slide for examination under a microscope.

1 Claim, 2 Drawing Sheets

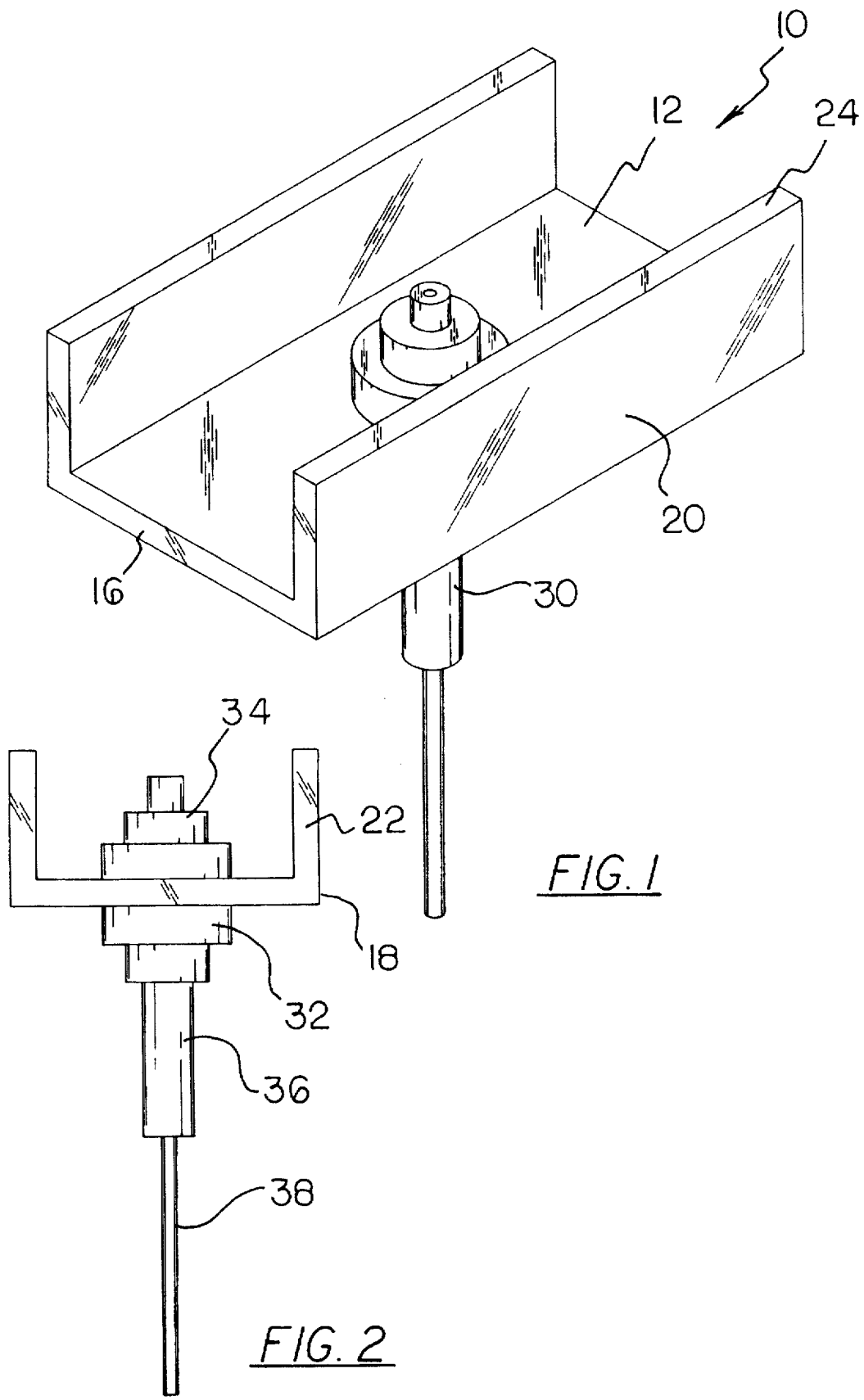

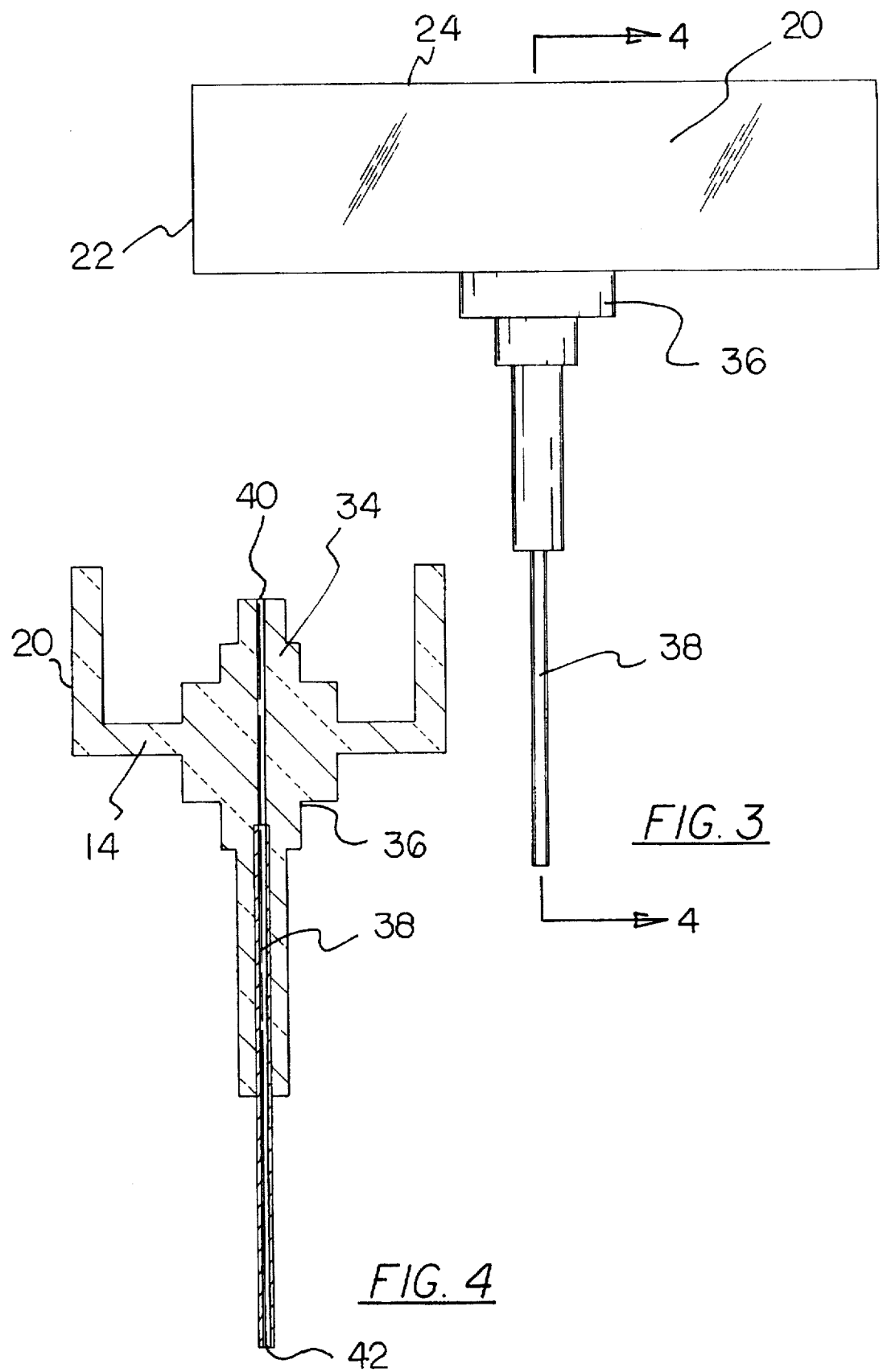

HEMATOLOGY BLOOD DISPENSING AND SMEARING DEVICE

BACKGROUND OF THE INVENTION

1. Field of the Invention

The present invention relates to a hematology blood dispensing and smearing device and more particularly pertains to dispensing and smearing a sample of blood on a slide for reviewing under a microscope with a hematology blood dispensing and smearing device.

2. Description of the Prior Art

The use of liquid dispensers is known in the prior art. More specifically, liquid dispensers heretofore devised and utilized for the purpose of dispensing liquids are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,344,666 to Levine discloses a liquid dispenser.

U.S. Pat. No. 4,412,548 to Hoch discloses a multiple sample needle assembly.

U.S. Pat. No. 4,407,843 to Sasaki et al. discloses a smear sample preparing method.

U.S. Pat. No. Des. 314,622 to Andersson et al. discloses the ornamental design for a transfer cannula.

U.S. Pat. No. 5,117,837 to Wanamaker et al. discloses a blood drawing apparatus.

U.S. Pat. No. 5,356,595 to Kanamori et al. discloses an automated smear generator.

U.S. Pat. No. 4,994,040 to Cameron discloses a through the needle catheter insertion device and technique.

While these devices fulfill their respective, particular objective and requirements, the aforementioned patents do not describe a hematology blood dispensing and smearing device for dispensing and smearing a sample of blood on a slide for reviewing under a microscope.

In this respect, the hematology blood dispensing and smearing device according to the present invention substantially departs from the conventional concepts and designs of the prior art, and in doing so provides an apparatus primarily developed for the purpose of dispensing and smearing a sample of blood on a slide for reviewing under a microscope.

Therefore, it can be appreciated that there exists a continuing need for new and improved hematology blood dispensing and smearing device which can be used for dispensing and smearing a sample of blood on a slide for reviewing under a microscope. In this regard, the present invention substantially fulfills this need.

SUMMARY OF THE INVENTION

In the view of the foregoing disadvantages inherent in the known types of liquid dispensers now present in the prior art, the present invention provides an improved hematology blood dispensing and smearing device. As such, the general purpose of the present invention, which will be described subsequently in greater detail, is to provide a new and improved hematology blood dispensing and smearing device and method which has all the advantages of the prior art and none of the disadvantages.

To attain this, the present invention essentially comprises a smearing member comprising a horizontal planar member having a generally rectangular configuration. The horizontal planar member has short end edges and long side edges. The horizontal member has a length of about 22 millimeters and a width of about 12 millimeters. The smearing member includes a pair of vertical planar members. The vertical planar members each have a generally rectangular configuration with short end edges and long side edges. Each vertical planar member has a length of about 22 millimeters and a height of about 6 millimeters. A lower side edge of each vertical planar member is integral with opposing long side edges of the horizontal planar member in an orthogonal orientation whereby the smearing member having a U-shaped configuration. The device includes a cannula portion comprising a main body secured within the horizontal planar member of the smearing member. The main body has an upper portion disposed above the horizontal planar member and a lower portion disposed below the horizontal planar member. The upper portion is disposed below upper side edges of the vertical planar members. The cannula portion includes an elongated tube having open ends. The elongated tube extends through the main body with an open upper end terminating at an end of the upper portion of the main body. An open lower end of the elongated tube extends outwardly of the lower portion of the main body.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hematology blood dispensing and smearing device which has all the advantages of the prior art liquid dispensers and none of the disadvantages.

It is another object of the present invention to provide a new and improved hematology blood dispensing and smearing device which may be easily and efficiently manufactured and marketed.

It is a further object of the present invention to provide a new and improved hematology blood dispensing and smearing device which is of durable and reliable construction.

An even further object of the present invention is to provide a new and improved hematology blood dispensing and smearing device which is susceptible of a low cost of manufacture with regard to both materials and labor, and which accordingly is then susceptible of low prices of sale to the consuming public, thereby making such a hematology blood dispensing and smearing device economically available to the buying public.

Still yet another object of the present invention is to provide a new and improved hematology blood dispensing and smearing device which provides in the apparatuses and methods of the prior art some of the advantages thereof, while simultaneously overcoming some of the disadvantages normally associated therewith.

Even still another object of the present invention is to provide a new and improved hematology blood dispensing and smearing device for dispensing and smearing a sample of blood on a slide for reviewing under a microscope.

Lastly, it is an object of the present invention to provide a new and improved hematology blood dispensing and smearing device including a smearing member. A cannula portion is secured within the smearing member for puncturing a closed collection tube to obtain a drop of blood to be smeared onto a slide for examination under a microscope.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the hematology blood dispensing and smearing device constructed in accordance with the principles of the present invention.

FIG. 2 is a front elevation view of the present invention.

FIG. 3 is a side elevation view of the present invention.

FIG. 4 is a cross-sectional view as taken along line 4—4 of FIG. 3. The same reference numerals refer to the same parts through the various Figures.

DESCRIPTION OF THE PREFERRED EMBODIMENT

With reference now to the drawings, and in particular, to FIGS. 1–4 thereof, the preferred embodiment of the new and improved hematology blood dispensing and smearing device embodying the principles and concepts of the present invention and generally designated by the reference number 10 will be described.

Specifically, it will be noted in the various Figures that the device relates to a new and improved hematology blood dispensing and smearing device for dispensing and smearing a sample of blood on a slide for reviewing under a microscope. In its broadest context, the device consists of a smearing member and a cannula portion. Such components are individually configured and correlated with respect to each other so as to attain the desired objective.

The device 10 includes a smearing member 12 comprising a horizontal planar member 14 having a generally rectangular configuration. The horizontal planar member 14 has short end edges 16 and long side edges 18. The horizontal member 12 has a length of about twenty-two millimeters and a width of about twelve millimeters. The smearing member 12 includes a pair of vertical planar members 20. The vertical planar members 20 each have a generally rectangular configuration with short end edges 22 and long side edges 24. Each vertical planar member 20 has a length of about twenty-two millimeters and a height of about six millimeters. A lower side edge 24 of each vertical planar member 20 is integral with opposing long side edges 18 of the horizontal planar member 14 in an orthogonal orientation whereby the smearing member 12 having a U-shaped configuration.

The device 10 includes a cannula portion 30 comprising a main body 32 secured within the horizontal planar member 14 of the smearing member 12. The main body 32 has an upper portion 34 disposed above the horizontal planar member 14 and a lower portion 36 disposed below the horizontal planar member 14. The upper portion 34 is disposed below upper side edges of the vertical planar members 20. The cannula portion 30 includes an elongated tube 38 having open ends. The elongated tube 38 extends through the main body 32 with an open upper end 40 terminating at an end of the upper portion 34 of the main body 32. An open lower end 42 of the elongated tube 38 extends outwardly of the lower portion 36 of the main body 32.

The device 10 is a new idea where the preparation of smears is made easier, safe and convenient with one single implement.

The device 10 utilizes the cannula portion 30 which is inserted in an unopened tube thru its stopper. The pressure produced by pressing the tube down on a slide pushes a drop of blood onto the slide. This eliminated the need to open the tube, thereby eliminating possible exposure from the blood sample. The device 10 eliminates the possible injury related to the use of another slide to spread the blood.

The drop of blood on the slide can then be made a smear by using either of the upper long side edges 24 of the spreading member 12. Holding the same blood tube at about 40–45 degree angle, the user then touches the drop of blood with the edge 24 of the spreading member 12. With one quick, continuous motion, a smear is made with a feathery edge at the end part of the smear.

The present invention uses a strong clear plastic for the spreading member 12. When the tube is pushed down the clear plastic provide a clear view of the drop of blood as it touches the surface of the slide. The cannula portion 30 is incorporated into the spreading member 12 through a central area, thereby making it as a unitary piece.

This device 10 is intended as a safe and easy means to puncture a closed collection tube to obtain a drop of blood through its stopper without having to remove the stopper. With this same device 10 a smear can be made by using the clear plastic smearing member 12 to smear the blood on a slide. This device 10 is a single use only and it is not intended for multiple specimens or to be cleaned and reused.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A hematology blood dispensing and smearing device for dispensing and smearing a sample of blood on a slide for reviewing under a microscope comprising, in combination:

a smearing member comprising a horizontal planar member having a generally rectangular configuration, the horizontal planar member having short end edges and long side edges, the horizontal member having a first length of about 22 millimeters and a width less than the first length of about 12 millimeters, the smearing member including at least one vertical planar member, the vertical planar member having a generally rectangular configuration with short end edges and long side edges, each vertical planar member having a length equal to the first length of about 22 millimeters and a height less than the first length of about 6 millimeters, a lower side edge of the vertical planar member being integral with opposing long side edge of the horizontal planar member in an orthogonal orientation whereby the smearing member having a U-shaped configuration;

said smearing member being constructed from a clear plastic;

a cannula portion comprising a main body secured with the horizontal planar member of the smearing member, the main body having an upper portion disposed above the horizontal planar member and a lower portion disposed below the horizontal planar member, the upper portion being disposed below upper side edge of the vertical planar member, the cannula portion including an elongated tube having open ends, the elongated tube extending through the main body with an open upper end terminating at an end of the upper portion of the main body, an open lower end of the elongated tube extending outwardly of the lower portion of the main body.

* * * * *